(12) United States Patent
Foster et al.

(10) Patent No.: US 11,026,716 B2
(45) Date of Patent: Jun. 8, 2021

(54) MEDICAL DEVICE SHAFT RESISTANT TO COMPRESSION AND/OR TENSION

(71) Applicant: BOSTON SCIENTIFIC SCIMED, INC., Maple Grove, MN (US)

(72) Inventors: Daniel J. Foster, Lino Lakes, MN (US); Kevin Robert Poppe, New Brighton, MN (US); Bradley S. Swehla, Eagan, MN (US); Christopher Jay Scheff, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 244 days.

(21) Appl. No.: 15/815,682

(22) Filed: Nov. 16, 2017

(65) Prior Publication Data
US 2018/0140323 A1 May 24, 2018

Related U.S. Application Data

(60) Provisional application No. 62/425,419, filed on Nov. 22, 2016.

(51) Int. Cl.
*A61B 17/34* (2006.01)
*A61M 25/01* (2006.01)
(Continued)

(52) U.S. Cl.
CPC ........ *A61B 17/3417* (2013.01); *A61F 2/2436* (2013.01); *A61F 2/962* (2013.01);
(Continued)

(58) Field of Classification Search
CPC ..... A61B 1/0051; A61B 1/0055; A61B 1/008; A61B 1/01; A61B 1/012; A61B 2017/003;
(Continued)

(56) References Cited

U.S. PATENT DOCUMENTS

| 3,674,014 A | 7/1972 | Tillander |
| 4,798,598 A | 1/1989 | Bonello et al. |

(Continued)

FOREIGN PATENT DOCUMENTS

| EP | 0778040 A2 | 6/1997 |
| JP | 06511163 A | 12/1994 |

(Continued)

OTHER PUBLICATIONS

International Search Report and Written Opinion dated Mar. 2, 2018 for International Application No. PCT/US2017/062113.

*Primary Examiner* — Robert A Lynch
(74) *Attorney, Agent, or Firm* — Seager, Tufte & Wickhem LLP

(57) ABSTRACT

Medical devices and methods for making and using medical devices are disclosed. An example medical device may be a medical device with increased compression resistance. The medical device may include an elongate shaft having a proximal end region, a distal end region, a lumen extending therethrough, and a tension resistance member extending at least partially between the proximal end region and the distal end region. An exoskeleton may be disposed along an outer surface of the shaft. The exoskeleton may include a plurality of discrete segments engaged with one another. At least one of the segments may be coupled to the tension resistance member.

15 Claims, 13 Drawing Sheets

(51) Int. Cl.

| | | |
|---|---|---|
| *A61F 2/962* | (2013.01) | |
| *A61F 2/24* | (2006.01) | |
| *A61M 25/00* | (2006.01) | |
| *A61F 2/954* | (2013.01) | |
| *A61M 39/10* | (2006.01) | |
| *A61B 17/00* | (2006.01) | |
| *A61B 17/04* | (2006.01) | |
| *A61B 17/16* | (2006.01) | |

(52) U.S. Cl.
CPC .... *A61M 25/0043* (2013.01); *A61M 25/0138* (2013.01); *A61M 25/0144* (2013.01); *A61B 17/1631* (2013.01); *A61B 2017/00526* (2013.01); *A61B 2017/0443* (2013.01); *A61F 2/954* (2013.01); *A61M 25/0136* (2013.01); *A61M 39/1011* (2013.01); *A61M 2025/0058* (2013.01); *A61M 2025/0059* (2013.01); *A61M 2025/0063* (2013.01)

(58) Field of Classification Search
CPC ........... A61B 2017/00305; A61B 2017/00336; A61B 17/3417; A61F 2/2436; A61F 2/954; A61M 25/0043; A61M 25/0138; A61M 25/0144; A61M 25/0147; A61M 2025/0059; A61M 2025/0063
See application file for complete search history.

(56) References Cited

U.S. PATENT DOCUMENTS

| | | |
|---|---|---|
| 4,955,384 A | 9/1990 | Taylor et al. |
| 4,985,022 A | 1/1991 | Fearnot et al. |
| 4,998,923 A | 3/1991 | Samson et al. |
| 5,003,989 A | 4/1991 | Taylor et al. |
| 5,095,915 A | 3/1992 | Engelson |
| 5,315,996 A | 5/1994 | Lundquist |
| 5,406,960 A | 4/1995 | Corso, Jr. |
| 5,437,288 A | 8/1995 | Schwartz et al. |
| 5,570,701 A | 11/1996 | Ellis et al. |
| 5,599,492 A | 2/1997 | Engelson |
| 5,746,701 A | 5/1998 | Noone |
| 5,749,837 A | 5/1998 | Palermo et al. |
| 5,769,796 A | 6/1998 | Palermo et al. |
| 5,772,609 A | 6/1998 | Nguyen et al. |
| 5,776,080 A | 7/1998 | Thome et al. |
| 5,833,632 A | 11/1998 | Jacobsen et al. |
| 5,902,254 A | 5/1999 | Magram |
| 5,931,830 A | 8/1999 | Jacobsen et al. |
| 5,951,494 A | 9/1999 | Wang et al. |
| 6,001,068 A | 12/1999 | Uchino et al. |
| 6,017,319 A | 1/2000 | Jacobsen et al. |
| 6,139,510 A | 10/2000 | Palermo |
| 6,273,876 B1 | 8/2001 | Klima et al. |
| 6,606,921 B2 | 8/2003 | Noetzold |
| 6,739,787 B1 | 5/2004 | Bystrom |
| 6,918,882 B2 | 7/2005 | Skujins et al. |
| 6,921,397 B2 | 7/2005 | Corcoran et al. |
| 7,055,656 B2 | 6/2006 | Drew |
| 7,074,197 B2 | 7/2006 | Reynolds et al. |
| 7,338,495 B2 | 3/2008 | Adams |
| 7,413,563 B2 | 8/2008 | Corcoran et al. |
| 7,533,906 B2 | 5/2009 | Luettgen et al. |
| 7,540,865 B2 | 6/2009 | Griffin et al. |
| 7,579,550 B2 | 8/2009 | Dayton et al. |
| 7,618,379 B2 | 11/2009 | Reynolds et al. |
| 7,625,364 B2 | 12/2009 | Corcoran et al. |
| 7,780,611 B2 | 8/2010 | Griego et al. |
| 7,784,376 B2 | 8/2010 | Wen |
| 7,824,345 B2 | 11/2010 | Euteneuer et al. |
| 7,841,994 B2 | 11/2010 | Skujins et al. |
| 7,850,623 B2 | 12/2010 | Griffin et al. |
| 7,854,109 B2 | 12/2010 | Zubiate et al. |
| 7,914,466 B2 | 3/2011 | Davis et al. |
| 7,914,467 B2 | 3/2011 | Layman et al. |
| 7,918,080 B2 | 4/2011 | Zubiate et al. |
| 7,993,286 B2 | 8/2011 | Reynolds et al. |
| 8,022,331 B2 | 9/2011 | Reynolds et al. |
| 8,047,236 B2 | 11/2011 | Perry |
| 8,048,004 B2 | 11/2011 | Davis et al. |
| 8,048,060 B2 | 11/2011 | Griffin et al. |
| 8,099,939 B2 | 1/2012 | Zubiate et al. |
| 8,100,031 B2 | 1/2012 | Zubiate et al. |
| 8,105,246 B2 | 1/2012 | Voeller et al. |
| 8,124,876 B2 | 2/2012 | Dayton et al. |
| 8,137,293 B2 | 3/2012 | Zhou et al. |
| 8,157,751 B2 | 4/2012 | Adams et al. |
| 8,182,465 B2 | 5/2012 | Griffin et al. |
| 8,192,422 B2 | 6/2012 | Zubiate et al. |
| 8,197,419 B2 | 6/2012 | Field et al. |
| 8,231,551 B2 | 7/2012 | Griffin et al. |
| 8,257,279 B2 | 9/2012 | Davis et al. |
| 8,292,829 B2 | 10/2012 | Griego et al. |
| 8,317,777 B2 | 11/2012 | Zubiate et al. |
| 8,376,865 B2 | 2/2013 | Forster et al. |
| 8,376,961 B2 | 2/2013 | Layman et al. |
| 8,377,035 B2 | 2/2013 | Zhou et al. |
| 8,397,481 B2 | 3/2013 | Zubiate et al. |
| 8,409,114 B2 | 4/2013 | Parins |
| 8,414,506 B2 | 4/2013 | Reynolds et al. |
| 8,425,408 B2 | 4/2013 | Boulais et al. |
| 8,443,692 B2 | 5/2013 | Zubiate et al. |
| 8,449,526 B2 | 5/2013 | Snyder et al. |
| 8,459,138 B2 | 6/2013 | Zubiate et al. |
| 8,475,366 B2 | 7/2013 | Boulais et al. |
| 8,485,992 B2 | 7/2013 | Griffin et al. |
| 8,535,219 B2 | 9/2013 | Smith et al. |
| 8,535,243 B2 | 9/2013 | Shireman |
| 8,551,020 B2 | 10/2013 | Chen et al. |
| 8,551,021 B2 | 10/2013 | Voeller et al. |
| 8,556,914 B2 | 10/2013 | Vrba |
| 8,608,648 B2 | 12/2013 | Banik et al. |
| 8,622,894 B2 | 1/2014 | Banik et al. |
| 8,636,716 B2 | 1/2014 | Griffin et al. |
| 8,656,697 B2 | 2/2014 | Zubiate et al. |
| 8,677,602 B2 | 3/2014 | Dayton et al. |
| 8,758,268 B2 | 6/2014 | Bown et al. |
| 8,784,337 B2 | 7/2014 | Voeller et al. |
| 8,795,202 B2 | 8/2014 | Northrop et al. |
| 8,795,254 B2 | 8/2014 | Layman et al. |
| 8,821,477 B2 | 9/2014 | Northrop et al. |
| 8,833,197 B2 | 9/2014 | Zubiate et al. |
| 8,845,552 B2 | 9/2014 | Greigo et al. |
| 8,864,654 B2 | 10/2014 | Kleiner et al. |
| 8,870,790 B2 | 10/2014 | Davis et al. |
| 8,900,163 B2 | 12/2014 | Jacobsen et al. |
| 8,915,865 B2 | 12/2014 | Jacobsen et al. |
| 8,932,235 B2 | 1/2015 | Jacobsen et al. |
| 8,936,558 B2 | 1/2015 | Jacobsen et al. |
| 8,939,916 B2 | 1/2015 | Jacobsen et al. |
| 8,945,096 B2 | 2/2015 | Zubiate et al. |
| 9,005,114 B2 | 4/2015 | Zubiate et al. |
| 9,011,318 B2 | 4/2015 | Choset et al. |
| 9,023,011 B2 | 5/2015 | Griffin et al. |
| 9,072,874 B2 | 7/2015 | Northrop et al. |
| 9,370,432 B2 | 6/2016 | Zubiate et al. |
| 9,375,234 B2 | 6/2016 | Vrba |
| 9,386,911 B2 | 7/2016 | Zubiate et al. |
| 9,387,308 B2 | 7/2016 | Hinchliffe et al. |
| 9,387,309 B2 | 7/2016 | Parodi et al. |
| 9,402,682 B2 | 8/2016 | Worrell et al. |
| 2003/0069520 A1 | 4/2003 | Skujins et al. |
| 2003/0069521 A1 | 4/2003 | Reynolds et al. |
| 2004/0220499 A1 | 11/2004 | Griego et al. |
| 2004/0243143 A1 | 12/2004 | Corcoran et al. |
| 2005/0080400 A1 | 4/2005 | Corcoran et al. |
| 2005/0090848 A1 | 4/2005 | Adams |
| 2005/0267444 A1 | 12/2005 | Griffin et al. |
| 2006/0111209 A1* | 5/2006 | Hinman ............... A61B 17/00 474/206 |
| 2006/0111615 A1* | 5/2006 | Danitz ............... A61B 1/00071 600/141 |
| 2006/0122537 A1 | 6/2006 | Reynolds et al. |

(56) References Cited

U.S. PATENT DOCUMENTS

| | | |
|---|---|---|
| 2006/0179966 A1 | 8/2006 | Kuo |
| 2006/0189896 A1 | 8/2006 | Davis et al. |
| 2007/0049902 A1 | 3/2007 | Griffin et al. |
| 2007/0066900 A1 | 3/2007 | O'Keeffe |
| 2007/0083132 A1 | 4/2007 | Sharrow |
| 2007/0100285 A1 | 5/2007 | Griffin et al. |
| 2007/0114211 A1 | 5/2007 | Reynolds et al. |
| 2007/0135734 A1 | 6/2007 | Reynolds et al. |
| 2007/0233043 A1 | 10/2007 | Dayton et al. |
| 2007/0244414 A1 | 10/2007 | Reynolds et al. |
| 2008/0064989 A1 | 3/2008 | Chen et al. |
| 2008/0077119 A1 | 3/2008 | Snyder et al. |
| 2008/0194994 A1 | 8/2008 | Bown et al. |
| 2008/0205980 A1 | 8/2008 | Zubiate et al. |
| 2008/0245173 A1 | 10/2008 | Schwerin et al. |
| 2008/0262474 A1 | 10/2008 | Northrop |
| 2009/0036833 A1 | 2/2009 | Parins |
| 2009/0043228 A1 | 2/2009 | Northrop et al. |
| 2009/0043283 A1 | 2/2009 | Turnlund et al. |
| 2009/0143768 A1 | 6/2009 | Parodi et al. |
| 2009/0156999 A1 | 6/2009 | Adams et al. |
| 2009/0171151 A1 | 7/2009 | Choset et al. |
| 2009/0312606 A1 | 12/2009 | Dayton et al. |
| 2010/0063480 A1 | 3/2010 | Shireman |
| 2010/0076266 A1 | 3/2010 | Boulais et al. |
| 2010/0080892 A1 | 4/2010 | O'Brien et al. |
| 2010/0145308 A1 | 6/2010 | Layman et al. |
| 2010/0249655 A1 | 9/2010 | Lemon |
| 2010/0286566 A1 | 11/2010 | Griffin et al. |
| 2010/0294071 A1 | 11/2010 | Zubiate et al. |
| 2010/0305475 A1 | 12/2010 | Hinchliffe et al. |
| 2011/0056320 A1 | 3/2011 | Zubiate et al. |
| 2011/0082443 A1 | 4/2011 | Griffin et al. |
| 2011/0152613 A1 | 6/2011 | Zubiate et al. |
| 2011/0184241 A1 | 7/2011 | Zubiate et al. |
| 2011/0257478 A1 | 10/2011 | Kleiner et al. |
| 2012/0160537 A1 | 6/2012 | Wen |
| 2013/0123912 A1 | 5/2013 | Tung et al. |
| 2014/0235361 A1 | 8/2014 | Forster et al. |
| 2017/0056171 A1* | 3/2017 | Cooper .............. A61M 25/0051 |

FOREIGN PATENT DOCUMENTS

| | | |
|---|---|---|
| JP | 5575840 B2 | 8/2014 |
| WO | 2006041612 A2 | 4/2006 |
| WO | 2006/073581 A2 | 7/2006 |

* cited by examiner

MEDICAL DEVICE SHAFT RESISTANT TO COMPRESSION AND/OR TENSION

CROSS-REFERENCE TO RELATED APPLICATIONS

This application claims the benefit of priority under 35 U.S.C. § 119 to U.S. Provisional Application Ser. No. 62/425,419, filed Nov. 22, 2016, the entirety of which is incorporated herein by reference.

TECHNICAL FIELD

The present disclosure pertains to medical devices, and methods for manufacturing medical devices. More particularly, the present disclosure pertains to medical devices including a shaft that is resistant to compression and/or to tension.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device with increased compression resistance is disclosed. The medical device comprises: an elongate shaft having a proximal end region, a distal end region, a lumen extending therethrough, and a tension resistance member extending at least partially between the proximal end region and the distal end region; an exoskeleton disposed along an outer surface of the shaft, the exoskeleton including a plurality of discrete segments engaged with one another; and wherein at least one of the segments is coupled to the tension resistance member.

Alternatively or additionally to any of the embodiments above, the plurality of discrete segments includes a first segment and a second segment.

Alternatively or additionally to any of the embodiments above, the first segment and the second segment alternate along the shaft.

Alternatively or additionally to any of the embodiments above, the first segment includes a barrel member.

Alternatively or additionally to any of the embodiments above, the second segment includes a bead member having a rounded proximal end and a rounded distal end.

Alternatively or additionally to any of the embodiments above, the rounded proximal end and the rounded distal end defines an axis of rotation that is centered on the bead member.

Alternatively or additionally to any of the embodiments above, the plurality of discrete segments are engaged with one another to exert tension on the shaft.

Alternatively or additionally to any of the embodiments above, the tension resistance member includes a metallic wire.

Alternatively or additionally to any of the embodiments above, the shaft is part of a delivery system for delivering an implantable medical device.

A delivery system is disclosed. The delivery system comprises: a compression-resistance inner shaft having a distal end region, a tension resistance member extending at least partially along the inner shaft, an outer surface, and an exoskeleton disposed along the outer surface; wherein the exoskeleton includes a plurality of bead members and a plurality of barrel members; wherein at least one of the bead members is attached to the tension resistance member; an implantable medical device coupled to the distal end region; and a sheath slidably disposed about the inner shaft.

Alternatively or additionally to any of the embodiments above, at least some of the bead members include a rounded proximal end and a rounded distal end.

Alternatively or additionally to any of the embodiments above, the rounded proximal end and the rounded distal end defines an axis of rotation that is centered on the bead member.

Alternatively or additionally to any of the embodiments above, the plurality of bead members and the plurality of barrel members are engaged with one another to exert tension on the inner shaft.

Alternatively or additionally to any of the embodiments above, the tension resistance member includes a metallic wire.

Alternatively or additionally to any of the embodiments above, the bead members and the barrel members alternate along the inner shaft.

Alternatively or additionally to any of the embodiments above, the inner shaft includes a pair of tension resistance members disposed along opposite sides of the inner shaft.

Alternatively or additionally to any of the embodiments above, the implantable medical device includes a prosthetic heart valve.

A system for delivering a prosthetic heart valve is disclosed. The system comprises: a compression-resistance inner shaft having a distal end region, a pair of tension resistance members extending along opposite sides of the inner shaft, an outer surface, and an exoskeleton disposed along the outer surface; wherein the exoskeleton includes a first member coupled to the pair of tension resistance members, a plurality of bead members, and a plurality of barrel members; a prosthetic valve coupled to the distal end region; and a sheath slidably disposed about the inner shaft.

Alternatively or additionally to any of the embodiments above, the plurality of bead members and the plurality of barrel members are engaged with one another to exert tension on the inner shaft.

Alternatively or additionally to any of the embodiments above, the bead members and the barrel members alternate along the inner shaft.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
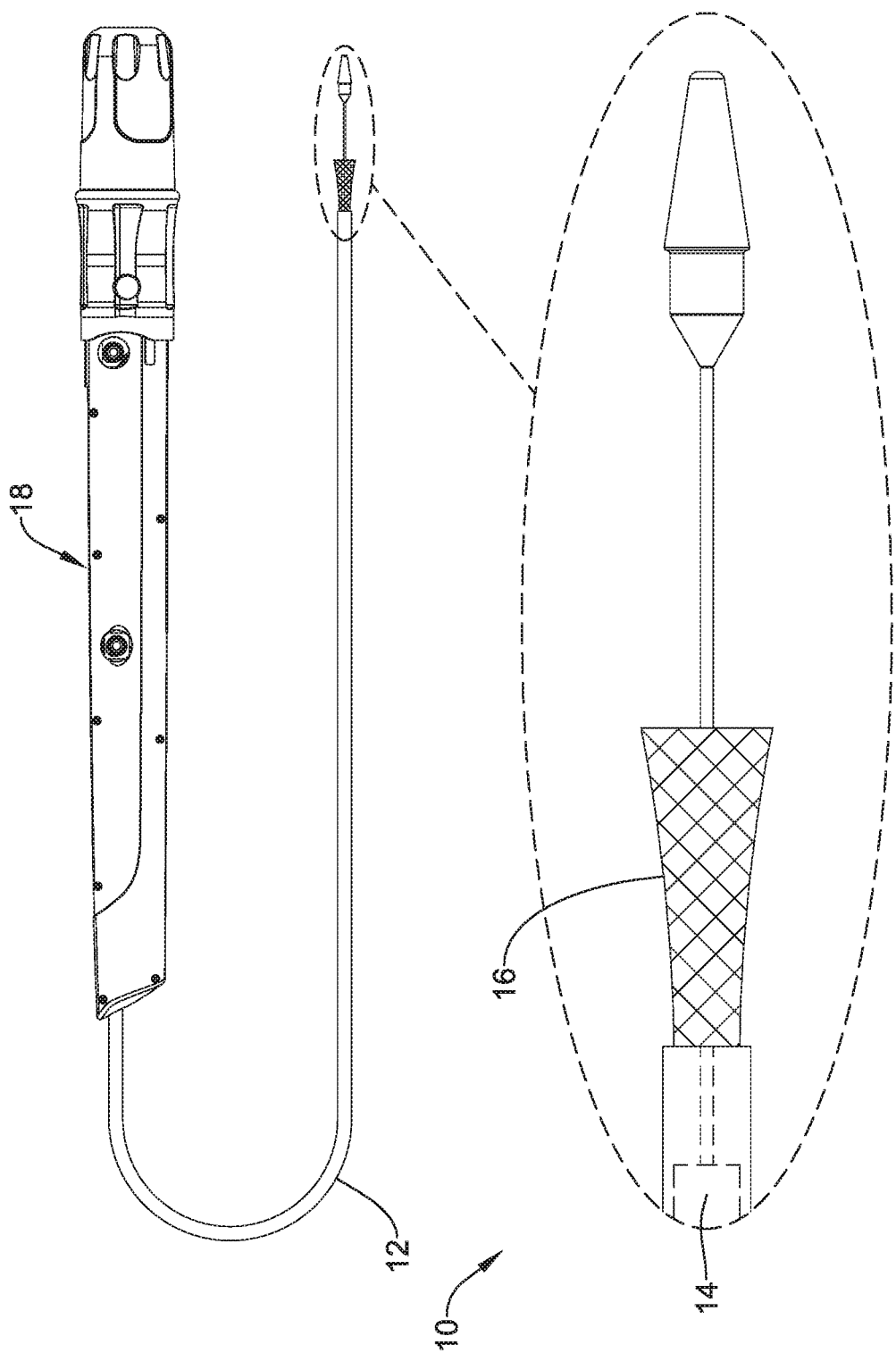
FIG. 1 is a side view of an example medical device system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Diseases and/or medical conditions that impact the cardiovascular system are prevalent throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to serious health condition and/or death if not dealt with properly. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve, replacement mitral valve, etc.). In addition, the devices disclosed herein may deliver the replacement heart valve percutaneously and, thus, may be much less invasive to the patient. The devices disclosed herein may also provide a number of additional desirable features and benefits as described in more detail below.

The figures illustrate selected components and/or arrangements of a medical device system 10, shown schematically in FIG. 1 for example. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of a medical implant 16, such as a replacement/prosthetic heart valve. This, however, is not intended to be limiting as the medical device system 10 may also be used for other interventions including valve repair, valvuloplasty, delivery of an implantable medical device (e.g., such as a stent, graft, etc.), and the like, or other similar interventions.

The medical device system 10 may generally be described as a catheter system that includes an outer sheath 12, an inner catheter 14 (a portion of which is shown in FIG. 1 in phantom line) extending at least partially through a lumen of the outer sheath 12, and a medical implant 16 (e.g., a replacement heart valve implant) which may be coupled to the inner catheter 14 and disposed within a lumen of the outer sheath 12 during delivery of the medical implant 16. In some embodiments, a medical device handle 18 may be disposed at a proximal end of the outer sheath 12 and/or the inner catheter 14 and may include one or more actuation mechanisms associated therewith. In other words, a tubular member (e.g., the outer sheath 12, the inner catheter 14, etc.) may extend distally from the medical device handle 18. In general, the medical device handle 18 may be designed to manipulate the position of the outer sheath 12 relative to the inner catheter 14 and/or aid in the deployment of the medical implant 16.

In use, the medical device system 10 may be advanced percutaneously through the vasculature to a position adjacent to an area of interest and/or a treatment location. For example, in some embodiments, the medical device system 10 may be advanced through the vasculature to a position adjacent to a defective native valve (e.g., aortic valve, mitral valve, etc.). Alternative approaches to treat a defective aortic valve and/or other heart valve(s) are also contemplated with the medical device system 10. During delivery, the medical implant 16 may be generally disposed in an elongated and low profile "delivery" configuration within the lumen and/or a distal end of the outer sheath 12, as seen schematically in FIG. 1 for example. Once positioned, the outer sheath 12 may be retracted relative to the medical implant 16 and/or the inner catheter 14 to expose the medical implant 16. In some instances, the medical implant 16 may be self-expanding such that exposure of the medical implant 16 may deploy the medical implant 16. Alternatively, the medical implant 16 may be expanded/deployed using the medical device handle 18 in order to translate the medical implant 16 into a generally shortened and larger profile "deployed" configuration suitable for implantation within the anatomy. When the medical implant 16 is suitably deployed within the anatomy, the medical device system 10 may be disconnected, detached, and/or released from the medical implant 16 and the medical device system 10 can be removed from the vasculature, leaving the medical implant 16 in place in a "released" configuration.

During delivery and/or deployment of an implantable medical device (e.g., the medical implant 16), portions of a medical device system (e.g., the medical device system 10) may be exposed to compressive forces and/or tension forces. If kept unchecked, the compressive forces could lead to compression and/or stretching of one or more components of the system. It may be desirable to utilize components in a medical delivery system (e.g., such as the medical device system 10 and/or other medical devices) that are resistant to compressive forces and/or to tension forces.

Figure 2:
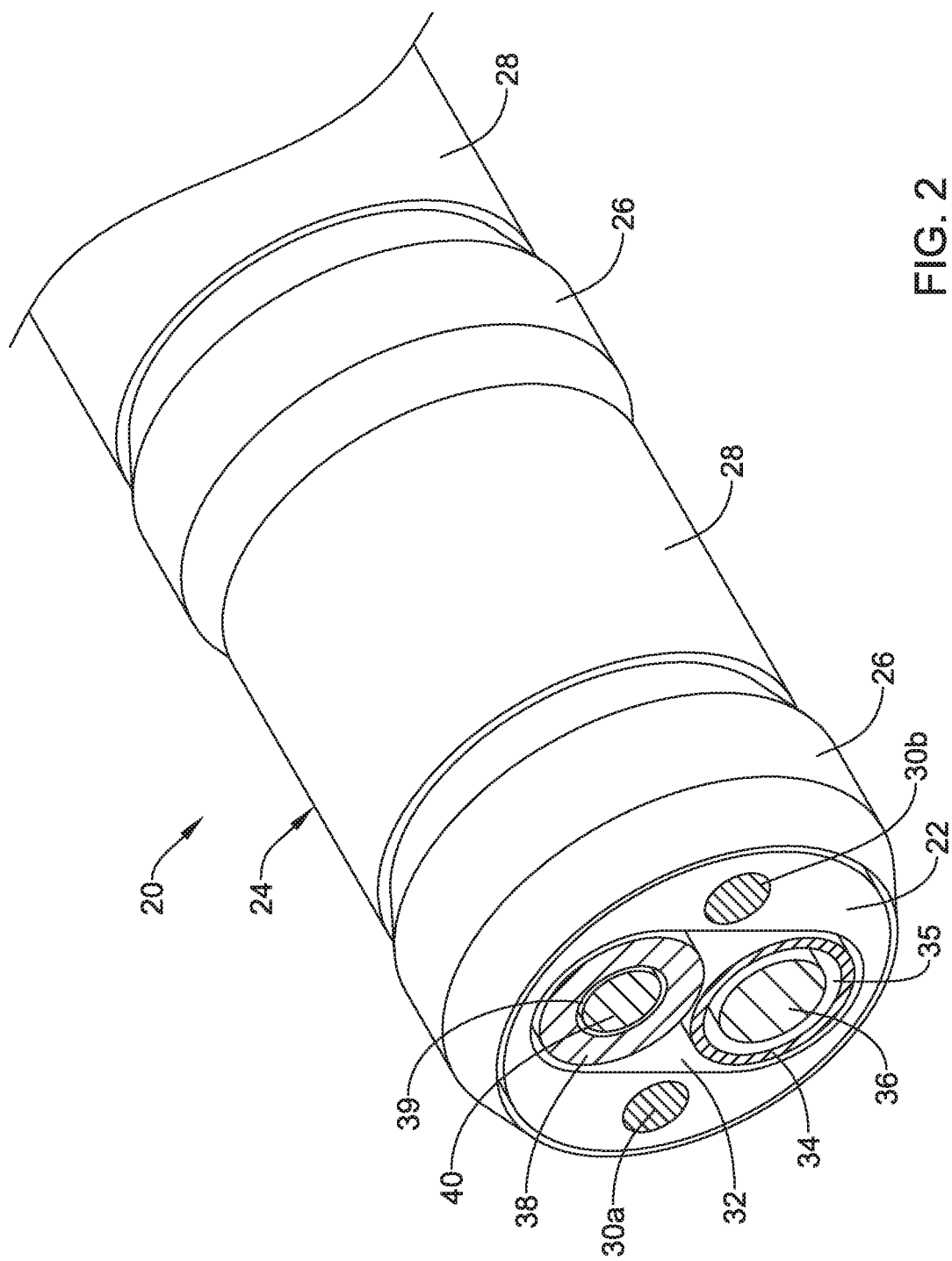
FIG. 2 is a partial cross-sectional view of a portion of an example shaft.

FIG. 2 illustrates a portion of an example shaft 20 that may have increased resistance to compressive forces (e.g., a "compression-resistant" shaft) and/or may have increased resistance to tension forces (e.g., a "tension-resistant" shaft). In some instances, the shaft 20 may be used as the inner catheter 14 in the medical device system 10 illustrated in FIG. 1. However, the shaft 20 may be other components of the medical device system 10, a component of a different medical device system (e.g., a stent delivery system, an angioplasty system, a biopsy system, etc.), any other medical device where compression and/or tension resistance may be desired, or the like.

The shaft 20 may include an inner member or liner 22. The inner liner 22 may include a number of features as discussed herein. An outer member or exoskeleton 24 may be disposed along the inner liner 22. The exoskeleton 24 may include a plurality of discrete members or articulating links. For example, the exoskeleton 24 may include a plurality of bead members 26 and a plurality of barrel members 28. Other discrete members are contemplated that may have differing shapes and/or configurations. In general, the discrete members (e.g., the bead members 26 and the barrel members 28) are engaged with one another and are designed to increase the compression resistance, the tension resistance, or both of the shaft 20 while also affording a desirable amount of flexibility and kink resistance such that the shaft 20 can be navigated through the anatomy.

As indicated above, the inner liner 22 may include a number of features. For example, the inner liners 22 may include one or more tension resistance members 30a/30b. The tension resistance members 30a/30b may take the form of a wire (e.g., a metallic wire), a braid, cable, stranded cable, a composite structure, or the like. In one example, the tension resistance members 30a/30b are both metallic wires. In another instance, the tension resistance members 30a/30b are both metallic braids. The braids may further includes an axial wire made from a suitable polymer or metal (e.g., aramid). The tension resistance members 30a/30b may be made from the same materials and/or have the same configuration. Alternatively, the tension resistance members 30a/30b may be different from one another. Furthermore, while FIG. 2 illustrates that the inner liner 22 includes two tension resistance members 30a/30b, this is not intended to be limiting. Other numbers of tension resistance members 30a/30b are contemplated such as one, three, four, five, six, seven, or more.

The inner liner 22 may also include a lumen 32. In some instances, a first tubular member 34 may be disposed within the lumen 32. The first tubular member may define a guidewire lumen 35, through which a guidewire 36 may extend. A second tubular member 38 may also be disposed within the lumen 32. The second tubular member 38 may define a lumen 39 through which an actuation mechanism 40 may extend. These are just examples. The inner liner 22 may vary in form. For example, the inner liner 22 may include a single lumen, multiple lumens, or lack a lumen.

Figure 3:
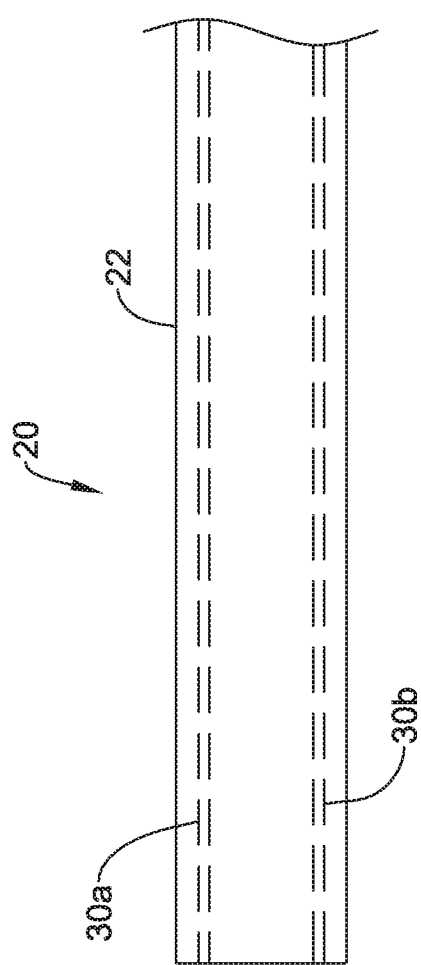
FIGS. 3-6 illustrate a portion of an example method for manufacturing a shaft.
Figure 4:
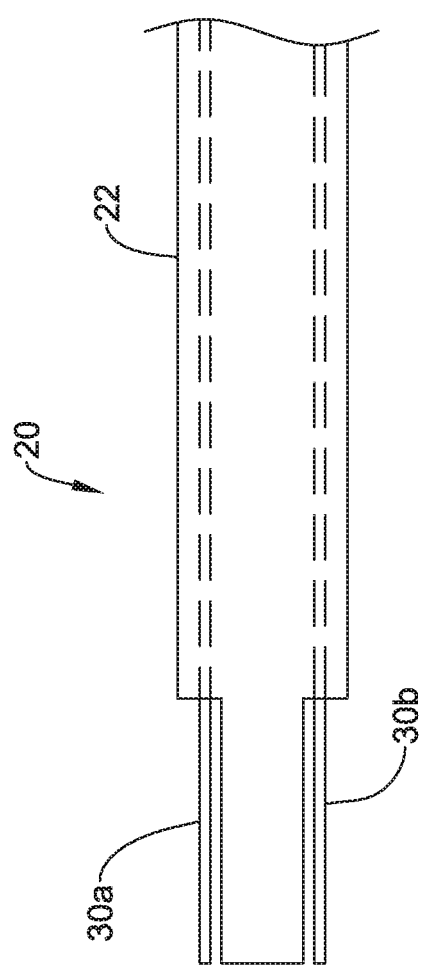
Figure 5:
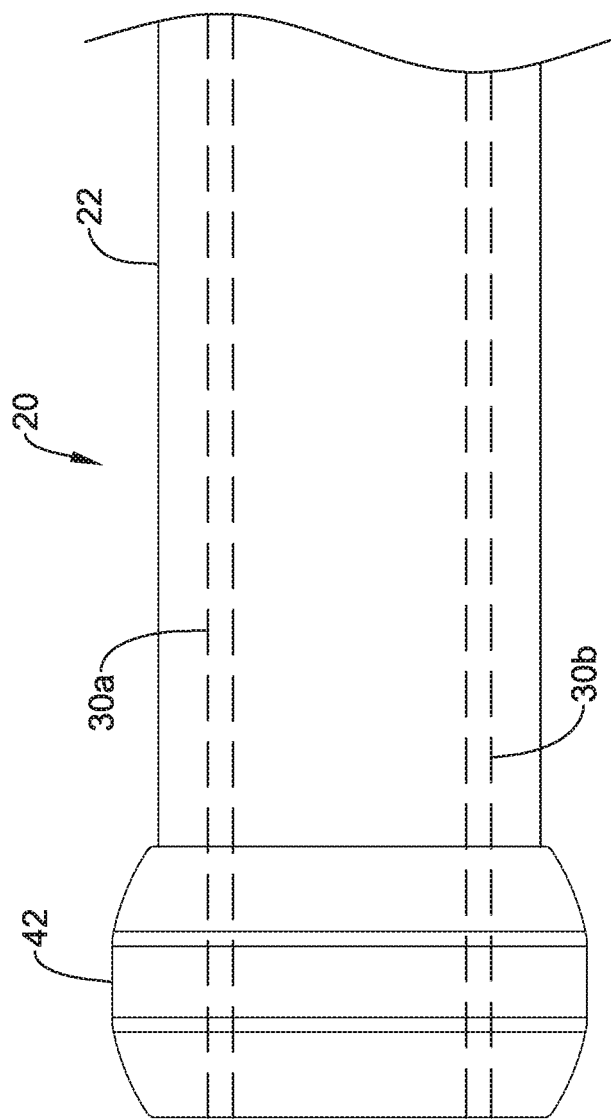

FIGS. 3-6 illustrate some of the processing steps for manufacturing the shaft 20. For example, FIG. 3 is a side view schematically depicting the inner liner 22 and the tension resistance members 30a/30b. A portion of the outer surface of the shaft 20 may be removed to expose the tension resistance members 30a/30b as shown in FIG. 4. An end member 42 may be disposed along the shaft 20 (e.g., along the region where a portion of the outer surface of the shaft 20 is removed) and coupled to the tension resistant members 30a/30b as shown in FIG. 5. The end member 42, which may be considered to be part of the exoskeleton 24, may be the same as or similar to one or more of the bead members 26, the same as or similar to one or more of the barrel members 28, a slight modification of one or more of the bead members 26 and/or the barrel members 28, or a structure that is different from the bead members 26 and/or the barrel members 28.

Figure 6:
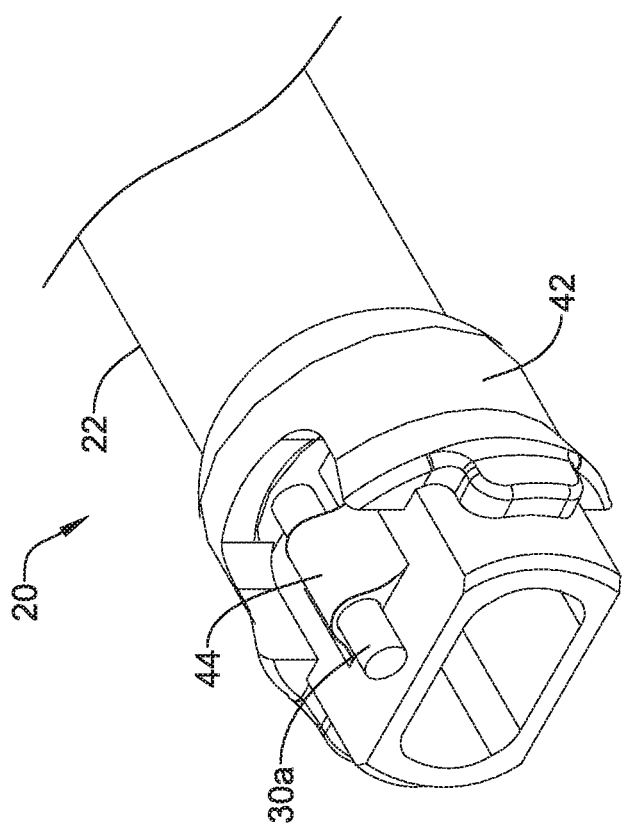

FIG. 6 illustrates one example configuration contemplated for the end member 42 and one possible mechanism for how the end member 42 may be coupled to the shaft 20, the inner liner 22 and/or the tension resistance members 30a/30b. In this example, the end member 42 includes one or more securing regions 44 that are designed to engage the tension resistance members 30a/30b. The securing regions 44 may be deformable so as to engage and mechanically lock with the tension resistance members 30a/30b. For example, the securing regions 44 may be crimped to mechanically lock the end member 42 to the tension resistance members 30a/30b. Other forms are contemplated for the end member 42 and other mechanisms are contemplated for securing the end member 42 to the tension resistance members 30a/30b.

Figure 7:
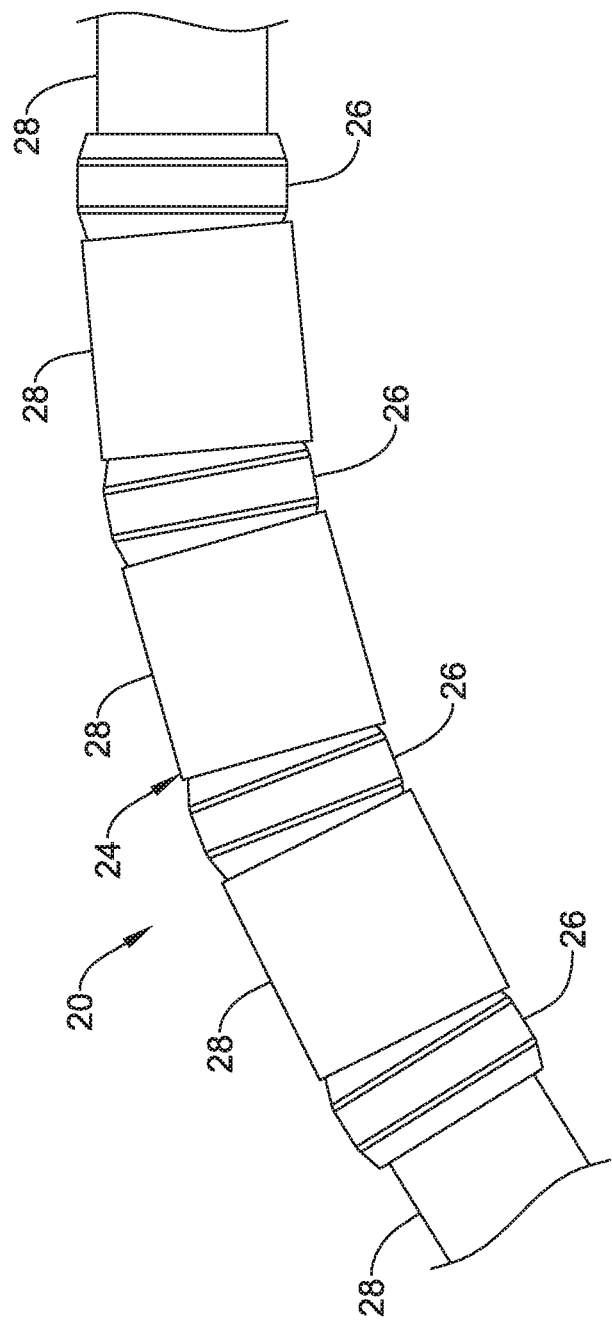
FIG. 7 is a side view of an example shaft.

After securing the end member 42 to the tension resistance members 30a/30b, the bead members 26 and the barrel members 28 may be disposed along the inner liner 22 to form the exoskeleton 24 as shown in FIG. 7. In some instances, tension may be applied to the end member 42 prior to forming the exoskeleton 24, during the formation of the exoskeleton 24, and/or at the end of forming the exoskeleton 24. The tension resistance members 30a/30b may prevent or other limit the inner liner 22 from stretching. Applying tension may cause the bead members 26 and the barrel members 28 to engage one another in a manner that limits compression of the inner liner 22.

The bead members 26 and the barrel members 28 may be arranged in a number of different manners along the inner liner 22. In at least some instances, the bead members 26 and the barrel members 28 alternate along the inner liner 22 (and/or along the shaft 20). Other arrangements and/or patterns are contemplated. At or adjacent to the proximal end of the shaft 20, one of the bead members 26, one of the barrel members 28, another member that may be similar to the bead members 26 and/or the barrel members 28, or another member that may be similar to the end member 42 may be secured to the proximal end of the tension resistance members 30a/30b. This may include removing a portion of the outer surface of the inner liner 22 to expose the tension resistance members 30a/30b (e.g., in a manner similar to what is described above) and securing the "proximal end member". When doing so, tension may be maintained along the exoskeleton 24. The "proximal end member" may be disposed within and/or otherwise coupled to a handle, hub, manifold, or the like.

The size of the bead members 26 and/or the barrel members 28 can also vary. In some instances, the shaft 20 uses a single size for the bead members 26 and a single size for the barrel members 28. Alternatively, some shafts may utilize differently sized bead members 26, differently sized barrel members 28, or both. It can be appreciated that as the length of the barrel members 28 increases, the bend radius of the shaft 20 also increases. For example, the barrel members 28 can have a length of about 0.05-3 inches, or about 0.09-2 inches. Some example bend radiuses for a number of different lengths of barrel members 28 are shown in Table 1.

TABLE 1

Example bend radiuses for shafts 20 with differently sized barrel members 28

| Length of barrel members (inches) | Bend Radius (inches) |
|---|---|
| 0.090 | 0.500 |
| 0.100 | 0.500 |
| 0.200 | 1.375 |
| 0.300 | 2.750 |
| 0.400 | 4.625 |
| 0.500 | 7.125 |
| 0.600 | 10.000 |
| 0.700 | 13.375 |
| 0.800 | 17.250 |
| 0.900 | 21.625 |
| 1.000 | 26.625 |
| 2.000 | 103.125 |

A number of additional variations are contemplated. For example, the diameter of the bead members 26 and/or the diameter of the barrel members 28 may also vary. It can be appreciated that as the diameter increases, the bend radius may also increase. Furthermore, the length of the barrel members 28 may change and/or vary, the thickness of the bead members 26 and/or barrel members 28 may change and/or vary, the clearance between the bead members 26 and/or barrel members 28 from the shaft 20 may change and/or vary, etc.

Figure 8:
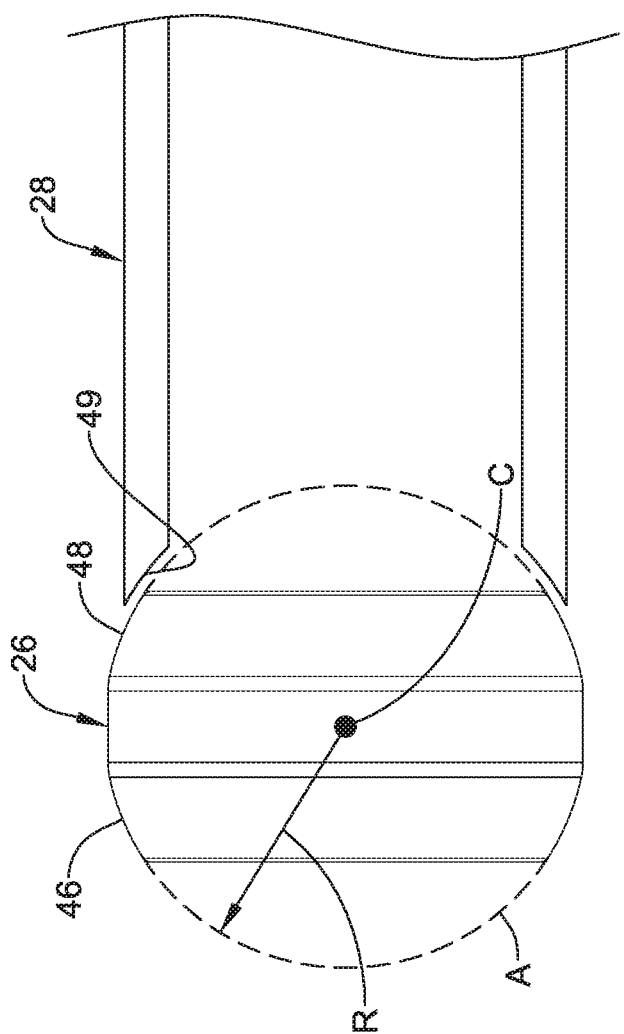
FIG. 8 is a side view of an example bead member and an example barrel member.

FIG. 8 illustrates one of the bead members 26 and one of the barrel members 28. Here it can be seen that the bead members 26 may include a rounded distal end region 46 and a rounded proximal end region 48. The rounded end regions 46/48 allow for some relative movement (e.g., axial rotation) of the bead members 26 relative to the barrel members 28. The barrel members 28 may also have a rounded inner surface 49 (it is noted that although only one end of the barrel member 28 is shown in FIG. 8, both ends may have rounded inner surfaces 49). The rounded inner surface 49 is designed to engage the rounded end regions 46/48 of the bead members 26. This allows the shaft 20 to be flexible and navigatable through the anatomy. The rounded end regions 46/48 may be considered to form an arc A. Extending the arc A about the bead member 26 may form a circle having a radius R and a center point C. The curvature of the rounded end regions 46/48 may be designed so that the arc A is centered at the center point C. This allows a desirable amount of relative movement between the bead members 26 and the barrel members 28 such that the shaft 20 is desirably flexible. In other words, the configuration of the bead members 26 (as well as the barrel members 28) is such that shaft 20 is compression resistance, resistant to tension forces (e.g., stretching), while still being flexible and bendable. Furthermore, engagement of the bead members 26 and the barrel members 28 (and/or that the center of rotation for the bead members 26, for example the center point C, is shared with the center of rotation of the inner liner 22) allows the shaft 20 to bend without changing the length of the inner liner 22. In other words, there is no relative axial movement between the inner liner 22 and the bead/barrel members 26/28.

Figure 9:
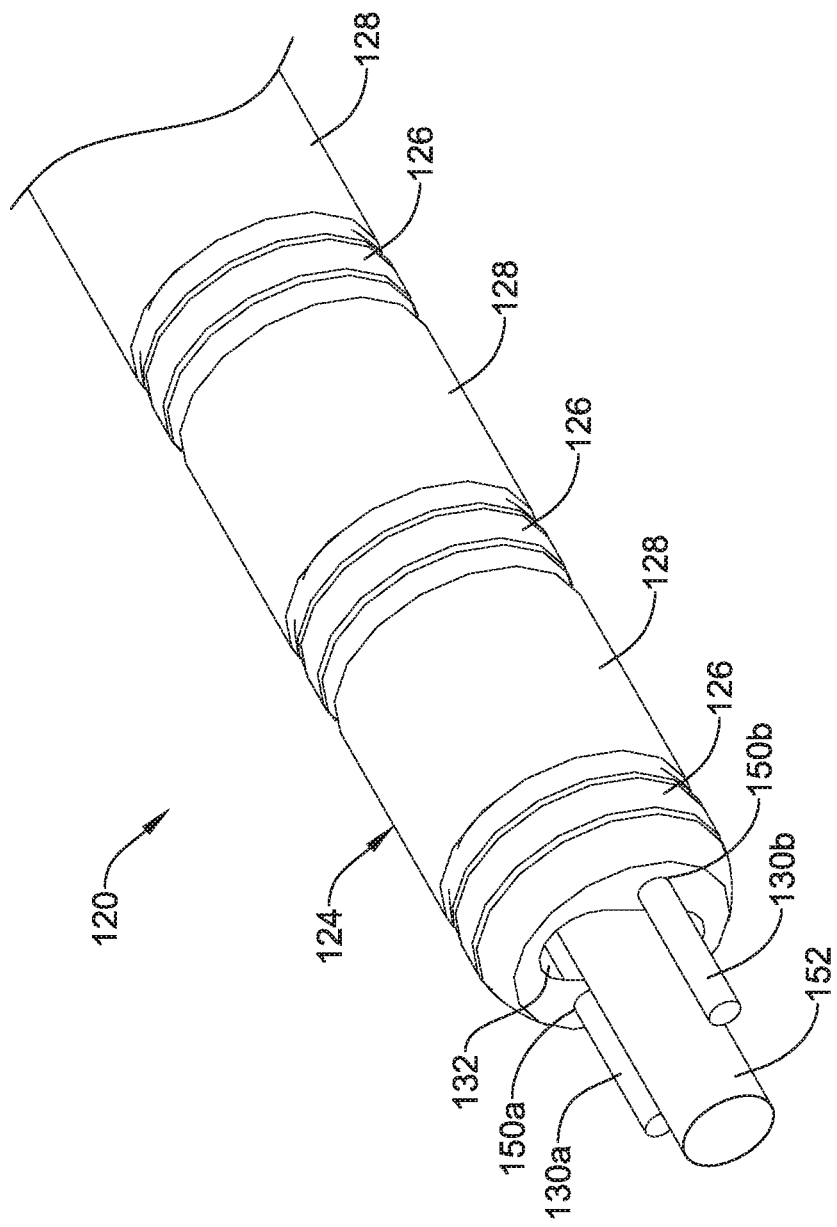
FIG. 9 is a perspective view of a portion of an example shaft.

FIG. 9 illustrates another example shaft 120 that may be similar in form and function to other shafts disclosed herein. The shaft 120 may include an exoskeleton 124. The exoskeleton 124 may include a plurality bead members 126 and a plurality of barrel members 128. In this example, one or more tension resistance members 130a/130b extend through the bead members 126 and the barrel members 120. More particularly, the bead members 126 and/or the barrel members 128 may include lumens 150a/150b through which the tension resistance members 130a/130b (which may simply be wires, braids, or the like) pass. The bead members 126 and/or the barrel members 128 may also include a lumen 132 through which other structures (e.g., such as a shaft 152) may extend. The shaft 152 may be a guidewire or other medical device. In such examples, the exoskeleton 124 may form or define the shaft 120. Alternatively, the shaft 152 may be a liner (e.g., similar to the inner liners disclosed herein). In at least some of these instances, the exoskeleton 126 can also provide tension resistance to the shaft 120 in addition to compression resistance. Thus, integrated tension members (e.g., in an inner liner) may not be needed in such examples, depending on needed tensile resistance.

Figure 10:
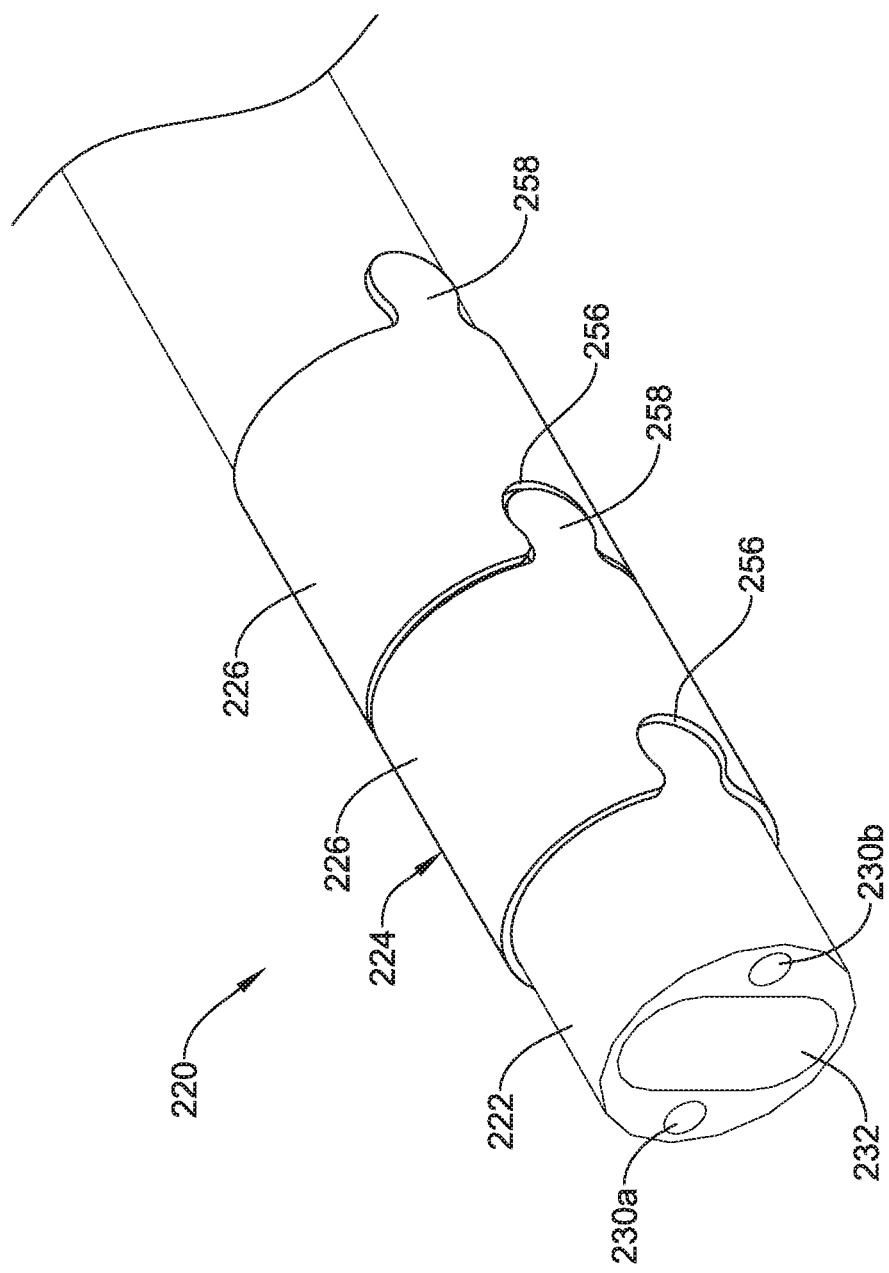
FIG. 10 is a perspective view of a portion of an example shaft.

FIG. 10 illustrates another example shaft 220 that may be similar in form and function to other shafts disclosed herein. The shaft 220 may include an inner liner 222. The inner liner 222 may include tension resistance members 230a/230b and a lumen 232. An exoskeleton 224 may be disposed along the inner liner 222. The exoskeleton 224 may include a plurality of interlocking members 226. Each of the interlocking members 226 may include a socket 256 and a projection 258. The projection 258 of one interlocking member 226 may engage the socket 256 of an adjacent interlocking member 226, and so on, to define the exoskeleton 224.

In some instances, the projections 258 may be axially aligned. When doing so, the shaft 220 may have one or more preferred bending directions (e.g., in directions oriented 90° or away from the aligned projections 258). In other words, the shaft 220 may be anisotropic. In other instances, one or more of the projections 258 may be rotated relative to one another. For example, adjacent projections 258 may be rotated 45-125° or about 90° relative to one another. This may result in shafts 220 that are equally bendable in substantially all directions or otherwise have no preferred bending directions (e.g., the shaft 220 is isotropic).

Figure 11:
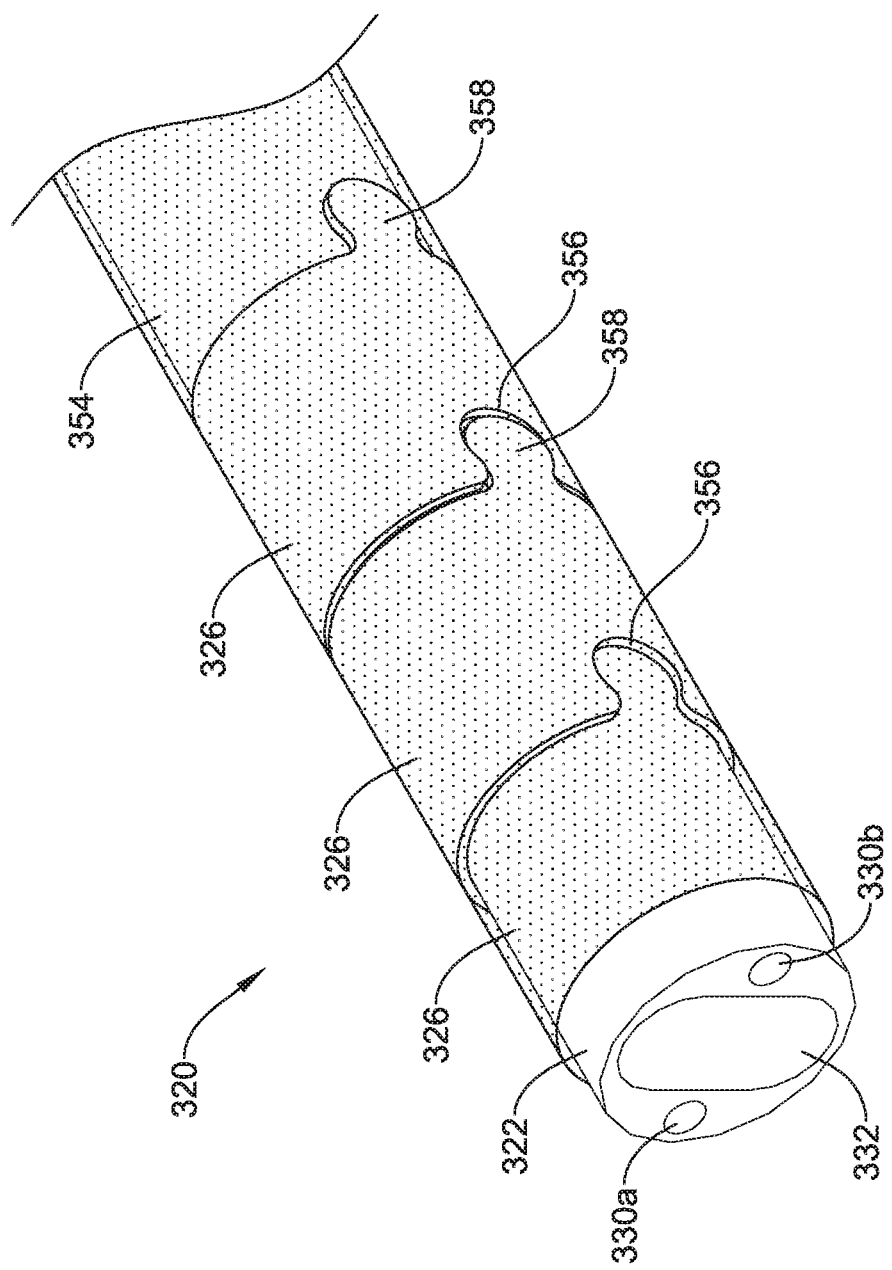
FIG. 11 is a perspective view of a portion of an example shaft.

FIG. 11 illustrates another example shaft 320 that may be similar in form and function to other shafts disclosed herein. The shaft 320 may include an inner liner 322. The inner liner 322 may include tension resistance members 330a/330b and a lumen 332. An exoskeleton 324 may be disposed along the inner liner 322. The exoskeleton 324 may include a plurality of interlocking members 326. Each of the interlocking members 326 may include a socket 356 and a projection 358. Like the interlocking members 226, the projection 358 of one interlocking member 326 may engage the socket 356 of an adjacent interlocking member 326, and so on, to define the exoskeleton 324. A covering 354 may be disposed along the interlocking members 326. The covering 354 may take the form of a sleeve, coil, braid, or the like. The covering may be designed to limit radial movement of the projections 358 or flexing of the projections 358 out from the sockets 356.

Figure 12:
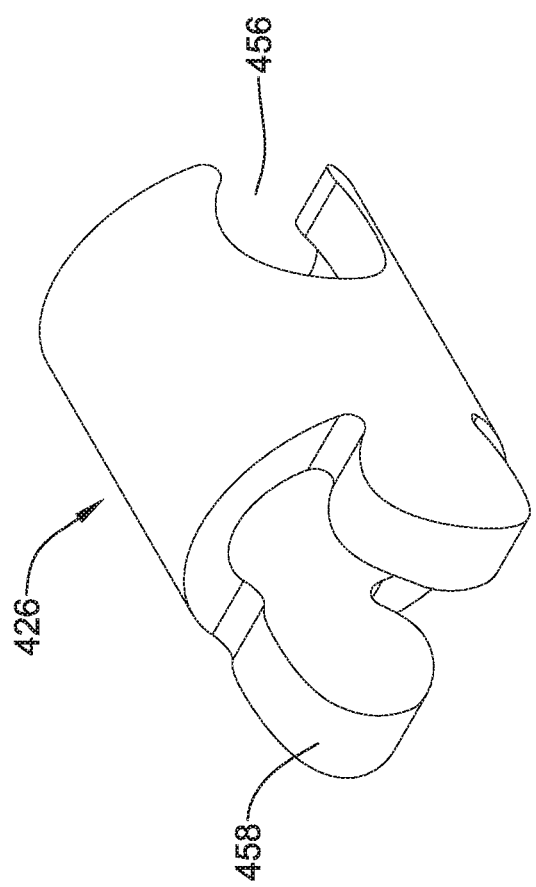
FIG. 12 is a perspective view of an example exoskeleton member.
Figure 13:
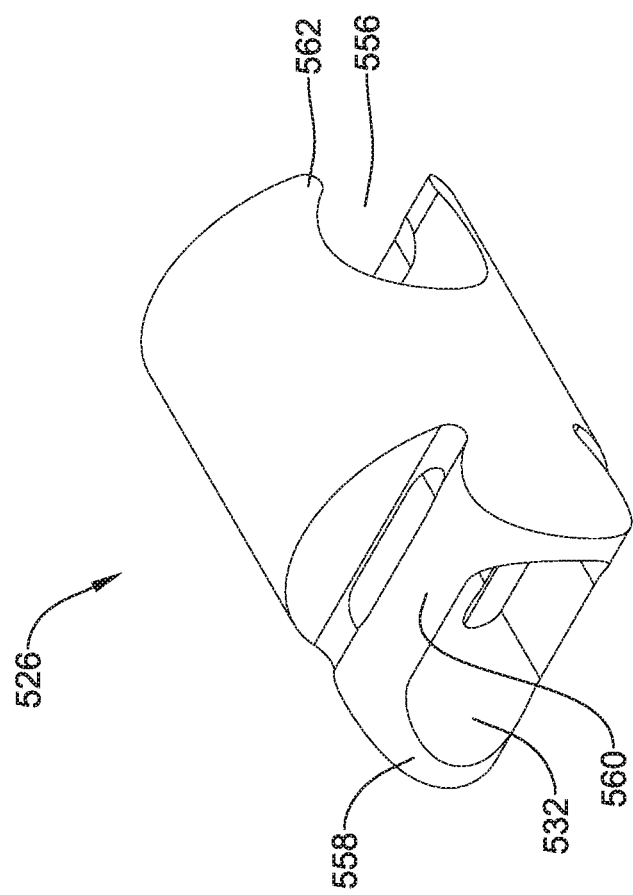
FIG. 13 is a perspective view of an example exoskeleton member.

FIGS. 12-13 illustrate some additional examples of members that may be used to form an exoskeleton similar to those disclosed herein. For example, FIG. 12 illustrates an interlocking member 426 having a socket region 456 and a projection 458. The socket region 456 is rotated relative to the projection 458. In addition, the projections 458 may have an increased thickness. This may reduce the likelihood of the projections 458 flexing out of the socket regions 456. FIG. 13 illustrates an interlocking member 526 having a socket 556 and a projection 558. The interlocking member 526 may include a lumen 532. In some instances, a strap region 560 may extend between the projections 558. In addition, the socket 556 may have a curved lip region 562. These features may reduce the likelihood of the projections 558 flexing out of the sockets 556. Other interlocking members are contemplated. These are just examples. In some of these and in other instances, the interlocking members (e.g., 226, 326, 426, 526, etc.) can also provide tension resistance. Thus, integrated tension members (e.g., in an inner liner) may not be needed in such examples, depending on needed tensile resistance.

The materials that can be used for the various components of the medical devices and/or systems disclosed herein (e.g., shaft 20 and/or other shafts disclosed herein) may include those commonly associated with medical devices. For simplicity purposes, the following discussion makes reference to the shaft 20. However, this is not intended to limit the devices and methods described herein, as the discussion may be applied to other shafts and/or components of the medical devices and/or systems disclosed herein including the various bead members, barrel members, etc.

The shaft 20 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high density polyethylene (HDPE), polyester, Marlex high-density polyethylene, Marlex low-density polyethylene, linear low density polyethylene (for example REXELL®), ultra-high molecular weight (UHMW) polyethylene, polypropylene, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the shaft may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the shaft in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the shaft 20 to achieve the same result.

In some embodiments, a degree of Magnetic Resonance Imaging (MRI) compatibility is imparted into the shaft. For example, the shaft 20 may include a material that does not substantially distort the image and create substantial artifacts (e.g., gaps in the image). Certain ferromagnetic materials, for example, may not be suitable because they may create artifacts in an MRI image. The shaft 20 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A medical device with increased compression resistance, comprising:
    an elongate shaft having a proximal end region, a distal end region, a lumen extending therethrough, and a tension resistance member extending at least partially between the proximal end region and the distal end region of the elongate shaft;
    an exoskeleton disposed along an outer surface of the elongate shaft, the exoskeleton including a plurality of discrete segments including first segments and second segments alternating with one another and engaged with one another along rounded surfaces forming arcs having a shared center; and
    wherein at least one of the plurality of discrete segments is coupled to the tension resistance member,
    wherein the tension resistance member extends within and through a central lumen of at least one discrete segment of the plurality of discrete segments.

2. The medical device of claim 1, wherein the first segments include a barrel member.

3. The medical device of claim 1, wherein the second segments include a bead member having a rounded proximal end and a rounded distal end.

4. The medical device of claim 3, wherein the rounded proximal end and the rounded distal end of the bead member define an axis of rotation that is centered on the bead member.

5. The medical device of claim 1, wherein the plurality of discrete segments are engaged with one another to exert tension on the elongate shaft.

6. The medical device of claim 1, wherein the tension resistance member includes a metallic wire.

7. The medical device of claim 1, wherein the elongate shaft is part of a delivery system for delivering an implantable medical device.

8. A delivery system, comprising:
    a compression-resistant inner shaft having a distal end region, a tension resistance member extending at least partially along the compression-resistant inner shaft, an outer surface, and within a central lumen of an exoskeleton disposed along the outer surface;
    wherein the exoskeleton includes a plurality of bead members alternating with a plurality of barrel members engaged with one another along rounded surfaces forming arcs having a shared center;
    wherein at least one of the plurality of bead members is attached to the tension resistance member;
    an implantable medical device coupled to the distal end region; and
    a sheath slidably disposed about the compression-resistant inner shaft.

9. The delivery system of claim 8, wherein at least some of the plurality of bead members include a rounded proximal end and a rounded distal end.

10. The delivery system of claim 9, wherein the rounded proximal end and the rounded distal end of the at least some bead members define an axis of rotation that is centered on the at least some of the plurality of bead members.

11. The delivery system of claim 8, wherein the plurality of bead members and the plurality of barrel members are engaged with one another to exert tension on the compression-resistant inner shaft.

12. The delivery system of claim 8, wherein the tension resistance member includes a metallic wire.

13. The delivery system of claim 8, wherein the plurality of bead members and the plurality of barrel members alternate along the compression-resistant inner shaft.

14. The delivery system of claim 8, wherein the compression-resistant inner shaft includes a pair of tension resistance members disposed along opposite sides of the compression-resistant inner shaft.

15. The delivery system of claim 8, wherein the implantable medical device includes a prosthetic heart valve.

* * * * *